United States Patent [19]

Doehner, Jr.

[11] Patent Number: 4,723,011
[45] Date of Patent: Feb. 2, 1988

[54] PREPARATION OF SUBSTITUTED AND DISUBSTITUTED-PYRIDINE-2,3-DICARBOXYLATE ESTERS

[75] Inventor: Robert F. Doehner, Jr., East Windsor, N.J.

[73] Assignee: American Cyanamid Company, Stamford, Conn.

[21] Appl. No.: 791,671

[22] Filed: Oct. 28, 1985

[51] Int. Cl.$^4$ .................................... C07D 213/803
[52] U.S. Cl. .................................. 546/250; 546/321; 546/318; 546/322
[58] Field of Search ..................... 546/250, 321

[56] References Cited

FOREIGN PATENT DOCUMENTS 2453305  6/1975  Fed. Rep. of Germany .

OTHER PUBLICATIONS

Newkome, "Pyridine and its Derivatives, Part 5" (1984) p. 170, Interscience Publisher, N.Y.
Bouvier, et al., Bull Soc. Chim. Fr. 711 (1963).
Bergmann, E. D. et al., J. Chem. Soc. C., 1968, pp. 1232–1235.
Klingsberg, E. "Pyridine and its Derivatives, Part One" (1960) Interscience Publishers, New York, pp. 417, 470, 471.
Chemical Abstracts, 49:15894b (1955).

*Primary Examiner*—Henry R. Jiles
*Assistant Examiner*—Dale A. Bjorkman
*Attorney, Agent, or Firm*—Susan H. Rauch; H. G. Jackson

[57]  ABSTRACT

Pyridine-2,3-dicarboxylates of Formula I

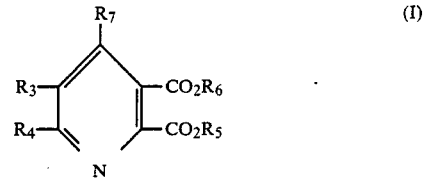

are prepared by reacting an alpha halo-beta keto ester of formula II

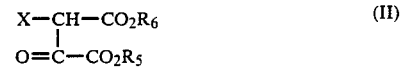

with an alpha, beta-unsaturated aldehyde or ketone of formula III

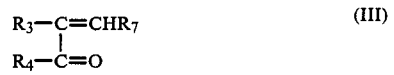

in the presence of a minimum of 2 molar equivalents of ammonium salt.

12 Claims, No Drawings

PREPARATION OF SUBSTITUTED AND DISUBSTITUTED-PYRIDINE-2,3-DICARBOXYLATE ESTERS

BACKGROUND OF THE INVENTION

Literature methods for preparing 5,6-dialkyl and 5,6-alkyl-arylpyridine-2,3-dicarboxylates are limited, often requiring oxidation of alkyl or aryl substituents at positions 2 and 3 in order to obtain diacids. R. Jones, J. Am. Chem. Soc. 73, 4380 (1951) describes a method in which reaction of a primary enamine yields 6-alkylpyridine2,3-dicarboxylates which contain electron withdrawing substituents such as $COCH_3$, $CN$ or $CO_2Et$ in the 5-position. This method cannot be used to prepare 5,6-dialkyl or alkylaryl pyridine 2,3-dicarboxylates because primary enamines without electron withdrawing substituents cannot readily be prepared, i.e., the reaction of ammonia with aliphatic ketones produces imines which do not tautomerize to enamines and, unless trapped in situ, polymerize. Other methods employing malononitriles such as those described in Japanese Pat. No. 78 69,835 and that of J. I. DeGraw J. Het. Chem. 19, 1461 (1982), can yield 5-alkyl and 5,6-dialkylpyridines but not with the desired 2,3-dicarboxylate substitution directly.

Pyridine-2,3-dicarboxylates are useful intermediates for the preparation of herbicidal 2-(2-imidazolin-2-yl) nicotinic acids, esters and salts such as those disclosed in European patent application No. 81103638.3 filed Dec. 1, 1981, as illustrated in Flow Diagram I below.

FLOW DIAGRAM I

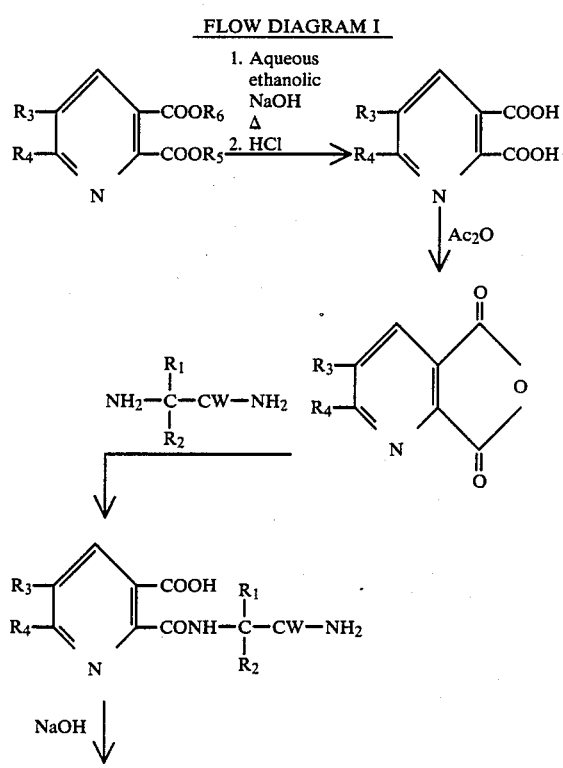

-continued
FLOW DIAGRAM I

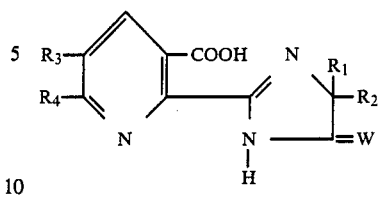

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl; W is O or S; and $R_3$ and $R_4$ are hydrogen, halogen $C_1$–$C_6$ straight or branched alkyl, alkenyl, or phenyl optionally substituted; $R_5$ and $R_6$ are each $C_1$–$C_4$ alkyl.

The condensation with $\alpha,\beta$-unsaturated systems by Michael addition of some halomethylene carbon nucleophiles activated by electron withdrawing groups is well documented, but the corresponding reaction of $\alpha$-halo-$\beta$-ketoesters such as that of diethyl 3-chloro-2-oxo-butanedioate with acrolein has been reported by P. Bouvier and H. Gault, Bull. Coc. Chim. Fr. 711 (1963), to result in mixtures.

It is an object of this invention to provide a method for the preparation of substituted and disubstituted pyridine-2,3-dicarboxylates and 2-alkyl nicotinates utilizing $\alpha$-halo-$\beta$-ketoesters and $\alpha,\beta$-unsaturated aldehydes or ketones in the presence of an ammonium salt.

SUMMARY OF THE INVENTION

The present invention is a novel method for the preparation of substituted and disubstituted pyridine 2,3-dicarboxylates of formula I

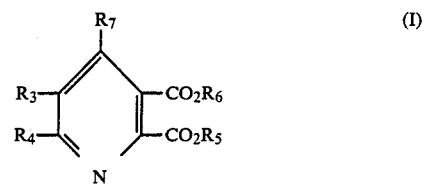

wherein $R_3$ is hydrogen, halogen, $C_1$–$C_6$ straight or branched alkyl, alkenyl, phenyl, or substituted-phenyl; $R_4$ and $R_7$ are each hydrogen, $C_1$–$C_6$ straight or branched alkyl, alkenyl, phenyl, or substituted-phenyl; $R_5$ and $R_6$ are each $C_1$–$C_4$ alkyl; comprising reacting an $\alpha$-halo-$\beta$-ketoester of formula II

wherein $R_5$ and $R_6$ are defined above and X is hologen preferably Cl with an $\alpha,\beta$-unsaturated aldehyde or ketone of formula III

wherein $R_3$, $R_4$ and $R_7$ are as described for in formula I above in the presence of a minimum of 2 molar equivalents of an ammonium salt in a solvent, in a temperature range of ambient temperature to the boiling point of the solvent until the reaction is essentially complete, as illustrated in Flow Diagram I below.

FLOW DIAGRAM I $$\underset{(II)}{\underset{O=C-CO_2R_5}{X-CH-CO_2R_6}} + \underset{(III)}{\underset{R_4-C=O}{R_3-C=CHR_7}}$$

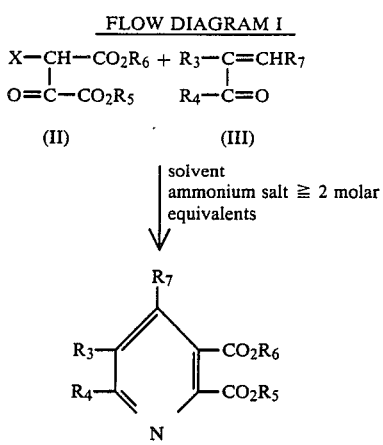

| solvent
| ammonium salt ≧ 2 molar
| equivalents

Solvents suitable for use in the method of this invention include: water, alcohols, chlorinated hydrocarbons, hydrocarbons, aromatic hydrocarbons, ethers, organic acids, esters, and aprotic solvents such as acetonitrile.

Thus, pyridine-2,3-dicarboxylates containing substituents in the 4-, 5- and 6-position may conveniently be prepared by admixing essentially equimolar amounts of a formula II α-halo-ketoester and a formula III α,β-unsaturated aldehyde or ketone with a minimum of 2 molar equivalents of an ammonium salt in a suitable solvent, and stirring the resulting reaction mixture at a temperature in the range of ambient temperature to the boiling point of the solvent, and preferably at reflux, until the reaction is essentially complete and isolating the thus-formed 4-substituted, 4,5-disubstituted, 5-substituted, 6-substituted or 5,6-disubstituted pyridine-2,3-dicarboxylate by standard laboratory techniques such as extraction, evaporation or column chromatography. Additionally, the method of the present invention is suitable for the preparation of substituted nicotinates of formula IV below

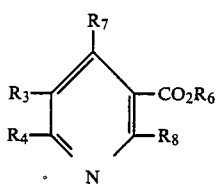

(IV)

wherein $R_3$, $R_4$, $R_6$ and $R_7$ are described for formula I; and $R_8$ is $C_1$–$C_4$ alkyl; comprising reacting an α-halo-β-ketoester of formula V $$\underset{O=C-R_8}{X-CH-CO_2R_6} \qquad (V)$$

wherein $R_6$ and $R_8$ are as defined for formula IV above, with an α,β-unsaturated aldehyde or ketone of formula III.

Formula IV nicotinates are also useful intermediates for the preparation of herbicidal 2-(2-imidazolin-2-yl) nicotinic acids, ester and salts by reaction with an aminocarboxamide in the presence of at least 3 equivalents of sulfur as described in U.S. Pat. No. 4,474,962 or by oxidation of $R_8$, for example, by the procedure described in U.S. Pat. No. 4,459,409, to yield the pyridine-2,3-dicarboxylic acid compounds of formula I above.

In order to facilitate a further understanding of the invention, the following examples are presented primarily for the purpose of illustrating certain more specific details thereof and the invention is not to be deemed limited thereby.

EXAMPLE 1

Preparation of diethyl 5-ethylpyridine-2,3-dicarboxylate a. A stirred mixture of ethacrolein, (4.2 g, 0.05 mol), diethyl 3-chloro-2-oxo-butanedioate, (11.2 g, 0.05 mol) and ammonium sulfamate, (15.4 g, 0.135 mol) in ethanol (37 mL) is heated at reflux. After 15 hours the mixture is cooled to room temperature and the solvent removed by distillation under reduced pressure. The residue is treated with water and extracted with ethyl acetate. The organic phase is separated and concentrated in vacuo and the residue purified by column chromatography on silica gel using 4:1 hexane-ethyl acetate as the eluent to give 10.8 g (75% yield) of the title product as an oil which is shown to be 95% pure by a gas chromatography assay.

b. The above reaction conducted with acetic acid as the solvent and utilizing diethyl 3-bromo-2-oxo-butanedioate in place of the chloro compound yields the same product in 48% yield.

EXAMPLE 2–19

Utilizing the procedure of Example 1 and substituting the appropriately substituted formula III α,β-unsaturated aldehyde or ketone for ethacrolein yields the pyridine-2,3-dicarboxylates listed in Table I below.

TABLE I

Preparation of Substituted Pyridine-2,3-Dicarboxylates

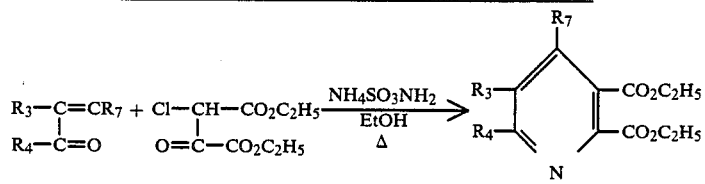

| | α,β-Unsaturated Aldehyde or Ketone | | | | | |
|---|---|---|---|---|---|---|
| Example | $R_3$ | $R_4$ | $R_7$ | % Yield | MP °C. | Anal OK for |
| 2 | H | H | H | 9.9 | oil | Known Compound (1) (NMR) |
| 3 | CH$_3$ | H | H | 58.5 | oil | C, H, N |
| 4 | n-C$_3$H$_7$ | H | H | 62.0 | oil | C, H, N |
| 5 | i-C$_3$H$_7$ | H | H | 66.0 | oil | C, H, N |

TABLE I-continued

Preparation of Substituted Pyridine-2,3-Dicarboxylates

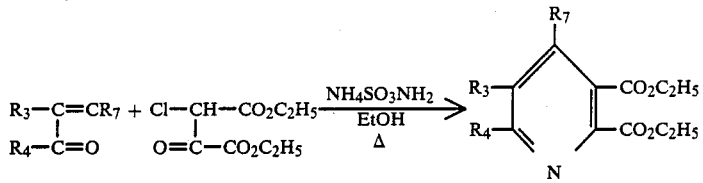

| Example | α,β-Unsaturated Aldehyde or Ketone | | | % Yield | MP °C. | Anal OK for |
|---|---|---|---|---|---|---|
| | $R_3$ | $R_4$ | $R_7$ | | | |
| 6 | n-$C_4H_9$ | H | H | 63.0 | oil | C, H, N |
| 7 | (2) HC≡CH—$CH_2$— | H | H | 47.5 | oil | C, H, N |
| 8 | (3) Cl | H | H | 55.0 | oil | C, H, N, Cl |
| 9 | (4) Br | H | H | 32.0 | oil | C, H, N, Br |
| 10 | phenyl | H | H | 24.8 | oil | C, H, N |
| 11 | H | H | $CH_3$ | 22.6 | oil | C, H, N |
| 12 | H | H | $C_2H_5$ | 26.0 | oil | C, H, N |
| 13 | H | H |  | 28.5 | 57–60 | C, H, N |
| 14 | H | H | phenyl | 32.0 | 71–76 | C, H, N |
| 15 | (5) H | phenyl | H | 52 | 54–56 | C, H, N |
| 16 | H | $CH_3$ | H | 27.5 | oil | C, H, N |
| 17 | $CH_3$ | H | $CH_3$ | 42.5 | 32–37 | C, H, N |
| 18 | $CH_3$ | $CH_3$ | H | 18.8 | oil | C, H, N |
| 19 | (6) 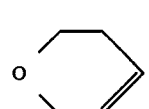 | | | 4.0 | 82.5–83.5 | C, H, N |

(1) CA 69: 86781q
(2) CA 69: 51617p (3) generated in situ from 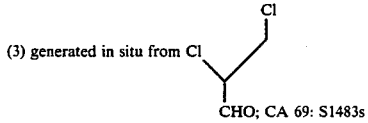; CA 69: 51483s (4) generated in situ from ; Smith et al, JACS 103, 1510 (1981)

(5) generated in situ from 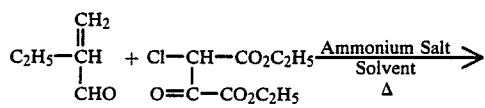; in lit.

(6) DE 3307-635-A

EXAMPLE 20

Efficacy of various ammonium salts and solvents for the preparation of diethyl 5-ethylpyridine-2,3-dicarboxylate $$\underset{\substack{|\\CHO}}{\overset{\substack{CH_2\\\|}}{C_2H_5-CH}} + \underset{\substack{|\\O=C-CO_2C_2H_5}}{Cl-CH-CO_2C_2H_5} \xrightarrow[\text{Solvent}]{\text{Ammonium Salt}} $$

-continued

[diethyl 5-ethylpyridine-2,3-dicarboxylate structure]

Equimolar amounts of ethacrolein and diethyl 3-chloro-2-oxo-butanedioate in various solvents in the presence of 2.7 molar equivalents of different ammonium salts are stirred at reflux for 15 hours. The products are isolated as in Example 1 and analyzed by gas chromatography. The results of these experiments which are summarized in Table II below, demonstrate the efficacy of various ammonium salts and solvents for the method of the present invention.

TABLE II

| Efficacy of Ammonium Salts and Solvents | | |
|---|---|---|
| Ammonium Salt | Solvent | % Yield of 5-ethylpyridine-2,3-dicarboxylate |
| $NH_4OCHO$ | $CH_3CN$ | 67 (crude) |
| $NH_4NO_3$ | $CH_3CN$ | Trace |
| $(NH_4)_2SO_4$ | $CH_3CN$ | 63.5 (crude) |
| $NH_4Cl$ | $CH_3CN$ | Trace |
| $NH_4OCOCH_3$ | $CH_3CN$ | 77 (crude) |
| $(NH_4)_3PO_4$ | $H_2O$ | 27.7 real |
| $NH_4OCOCH_3$ | Toluene | 50 (crude) |
| $NH_4OCOCH_3$ | $CH_2Cl_2$ | 64 (crude) |
| $NH_4OCOCH_3$ | THF | 51 (crude) |
| $NH_4OCOCH_3$ | cyclohexane | 44 (crude) |
| $(NH_4)_2SO_4$ | $H_2O$ | 70 (crude) |
| $NH_4SO_3NH_2$ | $CH_3CO_2H$ | 62 real |

EXAMPLE 21

Substitution of the equivalent amount of dipropyl 3-chloro-2-oxo-butanedioate for diethyl 3-chloro-2-oxo-butanedioate and use of propanol as solvent affords dipropyl 5-ethylpyridine-2,3-dicarboxylate. Dimethyl 3-chloro-2-oxobutanedioate gives dimethyl 5-ethylpyridine-2,3-dicarboxylate when the reaction is carried out in methanol.

EXAMPLE 22

Preparation of ethyl 5-ethyl-2-methylnicotinate

A mixture of ethacrolein (12.8 g 0.152 mole) and ammonium acetate (24.4 g 0.304 mole) in 50 cc acetonitrile is stirred at room temperature and a solution of ethyl 2-chloroacetoacetate (25 g 0.152 mole) in 30 cc acetonitrile is added dropwise over 15 minutes. The reaction mixture is heated at reflux for 16 hours, cooled, and partitioned between water and ethyl acetate. The organic phase is concentrated in vacuo and chromatographed on silica gel using 9:1 hexane-ethylacetate to afford 12.7 g of the title product.

What is claimed is:

1. A method for the preparation of substituted and disubstituted pyridine-2,3-dicarboxylates of formula I

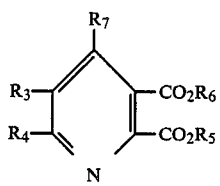

wherein $R_3$ is hydrogen, halogen, $C_1$-$C_6$ straight or branched alkyl, alkenyl, phenyl, or substituted-phenyl; $R_4$ and $R_7$ are each hydrogen, $C_1$-$C_6$ straight or branched alkyl, alkenyl, phenyl, or substituted-phenyl; and $R_5$ and $R_6$ are each $C_1$-$C_4$ alkyl; comprising reacting an α-halo-β-ketoester of formula II

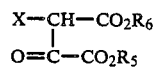

wherein $R_5$ and $R_6$ are defined above with an α,β-unsaturated aldehyde or ketone of formula III

wherein $R_3$, $R_4$ and $R_7$ are as described in formula I in the presence of a minimum of 2 molar equivalents of an ammonium salt in a solvent in a temperature range of ambient temperature to the boiling point of the solvent until the reaction is essentially complete.

2. A method according to claim 1 wherein the solvent is water, an alcohol, hydrocarbon, chlorinated hydrocarbon, aromatic hydrocarbon, ether, organic acid or ester, dimethyl sulfoxide, dimethylformamide, or acetonitrile.

3. A method according to claim 2 wherein the reaction is conducted in a temperature range of 30° C. to 140° C.

4. A method according to claim 3 wherein the formula II compound is diethyl 3-chloro-2-oxo-butanedioate.

5. A method according to claim 3 for the preparation of 5-substituted, 6-substituted and 5,6-disubstituted pyridine-2,3-dicarboxylates.

6. A method according to claim 3 for the preparation of diethyl 5-ethylpyridine-2,3-dicarboxylate.

7. A method according to claim 3 for the preparation of diethyl 5-methylpyridine-2,3-dicarboxylate.

8. A method according to claim 3 for the preparation of diethyl 5,6-dimethylpyridine-2,3-dicarboxylate.

9. A method according to claim 3 for the preparation of diethyl pyridine-2,3-dicarboxylate.

10. A method for the preparation of substituted nicotinates having the structure

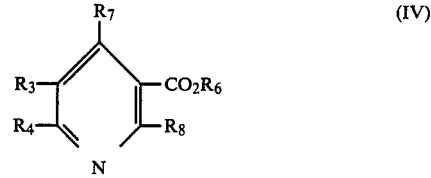

wherein $R_3$ is hydrogen, halogen, $C_1$-$C_6$ straight or branched alkyl, alkenyl, phenyl, or substituted-phenyl; $R_4$ and $R_7$ are each hydrogen, $C_1$-$C_6$ straight or branched alkyl, alkenyl, phenyl, substituted-phenyl; $R_6$ and $R_8$ are each $C_1$-$C_4$ alkyl; comprising reacting an α-halo-β-ketoester of formula V

wherein $R_6$ and $R_8$ are as defined for formula IV, with an α,β-unsaturated aldehyde or ketone of formula III

wherein $R_3$, $R_4$ and $R_7$ are as described in formula IV, in the presence of a minimum of 2 molar equivalents of an ammonium salt in a solvent in a temperature range of ambient temperature to the boiling point of the solvent until the reaction is essentially complete.

11. A method according to claim 10 for the preparation of ethyl 5-ethyl-2-methylnicotinate.

12. A method according to claim 10 for the preparation of ethyl 2,5-dimethylnicotinate.

* * * * *